(12) United States Patent
Inoue

(10) Patent No.: US 10,194,940 B2
(45) Date of Patent: Feb. 5, 2019

(54) LIVING CELL COLLECTION NEEDLE

(71) Applicant: Kitazato Medical Co., Ltd., Minato-ku, Tokyo (JP)

(72) Inventor: Futoshi Inoue, Fujinomiya (JP)

(73) Assignee: KITAZATO CORPORATION, Fuji-Shi, Shizuoka (JP)

(*) Notice: Subject to any disclaimer, the term of this patent is extended or adjusted under 35 U.S.C. 154(b) by 669 days.

(21) Appl. No.: 14/763,425

(22) PCT Filed: Jan. 25, 2013

(86) PCT No.: PCT/JP2013/051597
§ 371 (c)(1),
(2) Date: Jul. 24, 2015

(87) PCT Pub. No.: WO2014/115304
PCT Pub. Date: Jul. 31, 2014

(65) Prior Publication Data
US 2015/0327887 A1 Nov. 19, 2015

(51) Int. Cl.
*A61B 17/435* (2006.01)
*A61B 17/34* (2006.01)
*A61B 10/02* (2006.01)

(52) U.S. Cl.
CPC ........ *A61B 17/435* (2013.01); *A61B 10/0233* (2013.01); *A61B 17/3417* (2013.01);
(Continued)

(58) Field of Classification Search
CPC ........ A61B 17/425–17/435; A61M 2210/1441
(Continued)

(56) References Cited

U.S. PATENT DOCUMENTS

| 4,731,052 A | 3/1988 | Seitz, Jr. |
| 5,160,319 A | 11/1992 | Emery et al. |

(Continued)

FOREIGN PATENT DOCUMENTS

| CN | 201067425 Y | 6/2008 |
| JP | 2001-190560 A | 7/2001 |

(Continued)

OTHER PUBLICATIONS

Notification of Transmittal of Translation of the International Preliminary Report on Patentability (Forms PCT/IB/338 and PCT/IB/373) and the Written Opinion of the International Searching Authority (Form PCT/ISA/237) dated Aug. 6, 2015, by the International Bureau of WIPO in corresponding International Application No. PCT/JP2013/051597. (5 pages).

(Continued)

*Primary Examiner* — Catherine B Kuhlman
(74) *Attorney, Agent, or Firm* — Buchanan Ingersoll & Rooney PC

(57) ABSTRACT

A living cell collection needle has a hollow needle having a hollow body part, a hollow small-diameter front end part, a tapered part between the front end part and the hollow body part and decreasing in inner and outer diameters toward the front end of the needle, and a piercing cutting edge part at a front end of the small-diameter front end part; a hub fixed to a rear end portion of the hollow body part; an inner tube inside the hollow needle and a living cell sucking tube connected to a rear end portion of the inner tube. A rear end of the hollow needle is positioned inside the hub. The needle has a side tube with a front end portion inside the hub and communicating with the inside of the hollow needle and a rear end portion projecting rearward from the hub and liquid-tightly fixed to the hub.

20 Claims, 9 Drawing Sheets

(52) U.S. Cl.
    CPC ... *A61B 10/0283* (2013.01); *A61B 2017/3454* (2013.01); *A61B 2217/005* (2013.01)

(58) Field of Classification Search
    USPC .................................................. 600/33, 34
    See application file for complete search history.

(56) References Cited

U.S. PATENT DOCUMENTS

| | | | |
|---|---|---|---|
| 5,843,023 A | | 12/1998 | Cecchi |
| 2004/0225180 A1* | | 11/2004 | Junger ................ A61B 17/435 600/33 |
| 2005/0143619 A1* | | 6/2005 | Spittle ................ A61B 17/435 600/33 |
| 2006/0116605 A1* | | 6/2006 | Nakao ................ A61B 10/0266 600/566 |
| 2010/0081989 A1* | | 4/2010 | Berbers ................ A61B 17/435 604/44 |
| 2010/0179377 A1 | | 7/2010 | Hagby |
| 2010/0331883 A1* | | 12/2010 | Schmitz ............. A61B 10/0275 606/249 |

FOREIGN PATENT DOCUMENTS

| | | |
|---|---|---|
| JP | 2003-126106 A | 5/2003 |
| JP | 2006-055219 A | 3/2006 |
| JP | 3149897 U | 4/2009 |
| JP | 2010-534332 A | 11/2010 |

OTHER PUBLICATIONS

International Search Report (PCT/ISA/210) dated Feb. 19, 2013, by the Japanese Patent Office as the International Searching Authority for International Application No. PCT/JP2013/051597.

The extended European Search Report dated Oct. 27, 2016, in corresponding European Patent Application No. 13872423.2-1666. (8 pgs).

* cited by examiner

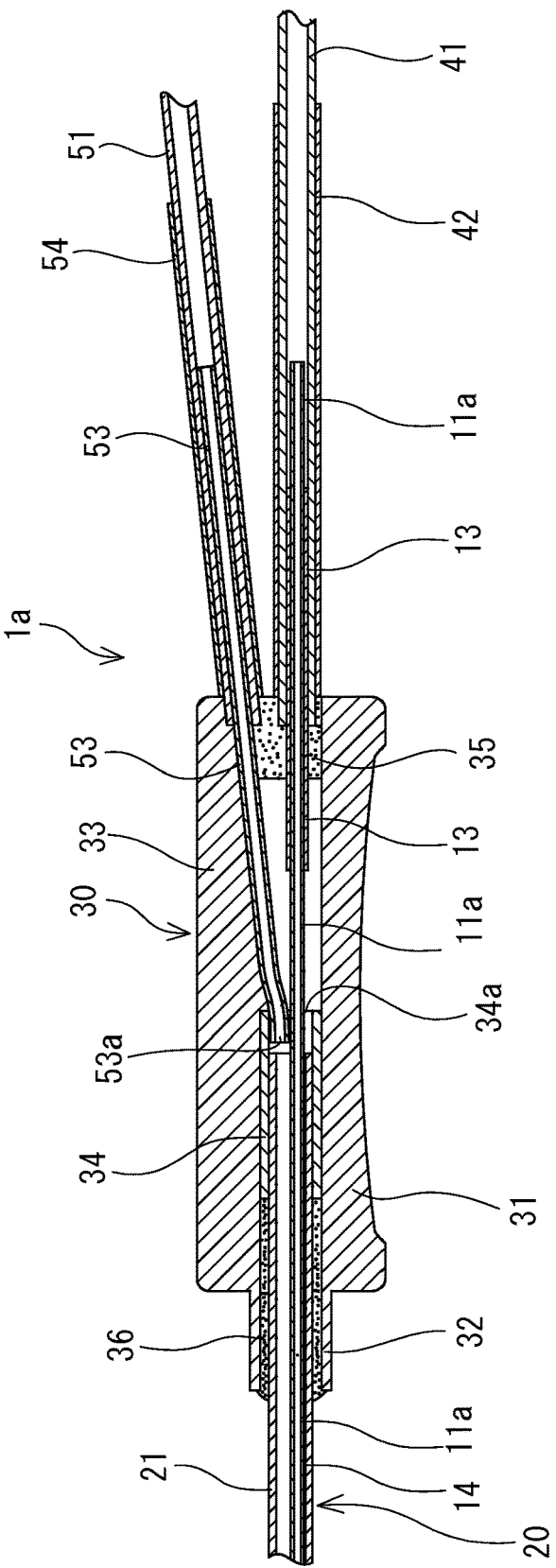

LIVING CELL COLLECTION NEEDLE

TECHNICAL FIELD

The present invention relates to a living cell collection needle for collecting oocytes or ova from follicles by piercing the living cell collection needle into an ovary.

BACKGROUND ART

Living cell collection needles for vaginally collecting oocytes or ova have been conventionally used. The living cell collection needle is described in a patent document 1 (Japanese Patent Application Laid-Open Publication No. 2003-126106). The tissue collection needle of the patent document 1 is composed of the hollow metal outer needle having the cutting edge provided at its front end, the hollow inner tube mounted inside the outer needle, and the branch connector having the means for fixing the rear end portion of the outer needle and that of the inner tube. The gap is formed between the hollow metal outer needle and the hollow inner tube. A portion of the branch connector disposed at the rear end portion of the metal outer needle allows the gap to have the liquid injection route open at the side of the axial direction of the hollow metal outer needle and that of the hollow inner tube and the open portion disposed at the side inward from the cutting face of the outer needle. In addition, the tissue sucking route passing through the inside of a portion of the branch connector disposed at the base of the outer needle is formed. The extension of the inner tube allows the front end portion of the inner tube to project forward from the cutting face of the outer needle.

As an ovum collection needle, the present applicant proposed the ovum collection instrument disclosed in a patent document 2 (Registered Japanese Utility Model Publication No. 3149897).

The living cell collection needle 1 of the patent document 2 has the hollow needle 2 composed of the hollow body part 22 extended by a predetermined length, the hollow small-diameter front end part 21 extended to the front side of the living cell collection needle from the body part 22 and having a shorter length and a smaller diameter than the hollow body part 22 and the hub 34 fixed to the rear end portion of the body part 22 of the hollow needle 2. In addition, formed at the tip of the hollow small-diameter front end part 21, the living cell collection needle 1 has the cutting edge part 24 composed of the piercing cutting face 23 and the curved side portion 54 curved toward the cutting face 23. The hollow small-diameter front end part 21 is coated with the low-friction substance. The hub 34 has the marker 38 associated with the direction of the cutting face 23.

PRIOR ART DOCUMENTS

Patent Documents

Patent document 1: Japanese Patent Application Laid-Open Publication No. 2003-126106
Patent document 2: Registered Japanese Utility Model Publication No. 3149897

SUMMARY OF THE INVENTION

Problems to be Solved by the Invention

The tissue collection needle of the patent document 1 is excellent in the return efficiency of the cleaning liquid in collecting ova from the ovary. The ovum collection needle of the patent document 2 relieves pain given to a subject in performing an ovum collection operation and allows an ovum collection person to easily perform the ovum collection operation.

As a result of the present inventors' examinations, they have found that the needle does not necessarily have to return the cleaning liquid supplied to the ovary and is only required to inject a collection auxiliary liquid into the ovary. Based on this finding, the present inventors have keenly studied about the ovum collection instrument which relieves pain given to the subject in performing the ovum collection operation and is capable of easily injecting the collection auxiliary liquid to the ovary of the subject and easily collecting living cells.

The present inventors have improved conventional ovum collection needles and thus it is an object of the present invention to provide a living cell collection needle which relieves pain given to a subject in performing an ovum collection operation, is capable of easily injecting a collection auxiliary liquid to an ovary of a subject, and allows a person who collects oocytes and ova to easily to perform a collection operation.

Means for Solving the Problems

The means for achieving the above-described object is as described below.

A living cell collection needle for collecting oocytes or ova from a human ovary comprises a hollow needle having a hollow body part extended by a predetermined length, a hollow small-diameter front end part extended from said hollow body part toward a front end of said living cell collection needle and having a shorter length and a smaller diameter than said hollow body part, a tapered part positioned between said hollow small-diameter front end part and said hollow body part and decreasing toward said hollow small-diameter front end part in outer and inner diameters thereof, and a piercing cutting edge part formed at a front end of said hollow small-diameter front end part; a hub fixed to a rear end portion of said hollow body part of said hollow needle; an inner tube which is accommodated inside said hollow needle, whose front end is positioned inside said tapered part or inside a front end portion of said hollow body part, and whose rear end portion penetrates through said hub and is fixed to said hub; and a living cell sucking tube connected to a rear end portion of said inner tube, wherein a rear end of said hollow needle is positioned inside said hub; said living cell collection needle has a side tube whose front end portion is positioned inside said hub and communicates with said inside of said hollow needle and whose rear end portion projects rearward from said hub and is liquid-tightly fixed to said hub; and a collection auxiliary liquid supply tube is connected to said side tube.

BRIEF DESCRIPTION OF THE DRAWINGS

FIG. 11 is an enlarged sectional view of the hub part of the hollow needle of the living cell collection needle of still another embodiment of the present invention.

MODE FOR CARRYING OUT THE INVENTION

Figure 1:
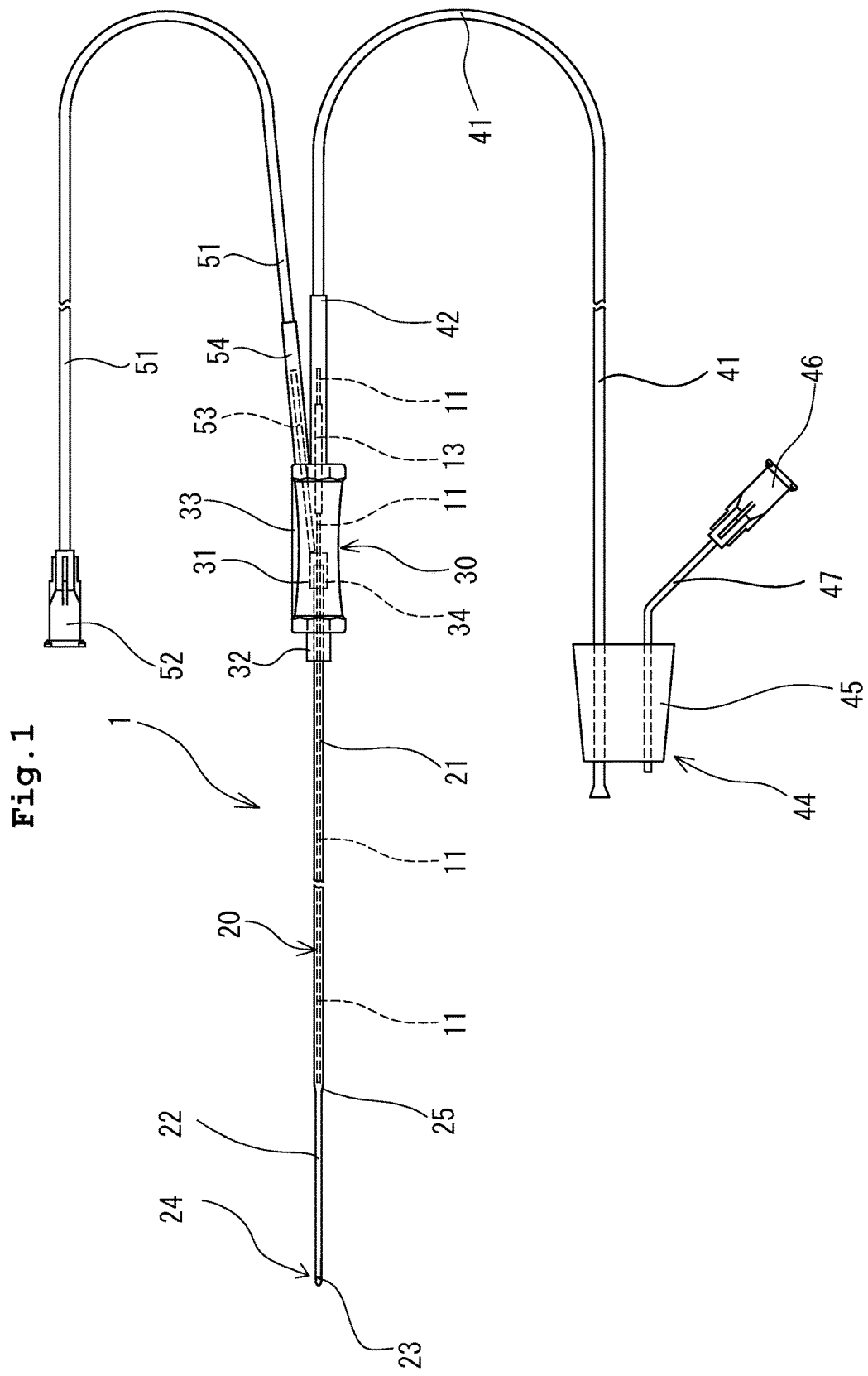
FIG. 1 is a partly abbreviated front view of one embodiment of a living cell collection needle of the present invention.

The living cell collection needle of the present invention will be described below by using embodiments shown in the drawings.

A living cell collection needle 1 is intended to collect oocytes or ova from a human ovary. The living cell collection needle 1 has a hollow needle 20 having a hollow body part 21 extended by a predetermined length, a hollow small-diameter front end part 22 extended from the hollow body part 21 toward a front end of the living cell collection needle 1 and having a shorter length and a smaller diameter than the hollow body part 21, a tapered part 25 positioned between the hollow small-diameter front end part 22 and the hollow body part 21 and decreasing toward the hollow small-diameter front end part 22 in its outer and inner diameters, and a piercing cutting edge part 24 formed at a front end of the hollow small-diameter front end part 22; a hub 30 fixed to a rear end portion of the hollow body part 21 of the hollow needle 20; an inner tube 11 which is accommodated inside the hollow needle 20, whose front end is positioned inside the tapered part 25 or inside a front end portion of the hollow body part 21, and whose rear end portion penetrates through the hub 30 and is fixed to the hub 30; and a living cell sucking tube 41 connected to a rear end portion of the inner tube 11.

A rear end of the hollow needle 20 is positioned inside the hub 30. The living cell collection needle 1 has a side tube 53 whose front end portion is positioned inside the hub 30 and communicates with the inside of the hollow needle 20 and whose rear end portion projects rearward from the hub 30 and is liquid-tightly fixed to the hub 30. A collection auxiliary liquid supply tube 51 is connected to the side tube 53.

The living cell collection needle of the present invention collects ova from follicles through a vagina. As shown in FIG. 1, the living cell collection needle 1 of the present invention has the hollow needle 20, the hub 30 fixed to the rear end portion of the hollow needle 20, and the inner tube 11 which is accommodated inside the hollow needle 20 and a rear end of which projects from the hub 30.

Figure 2:
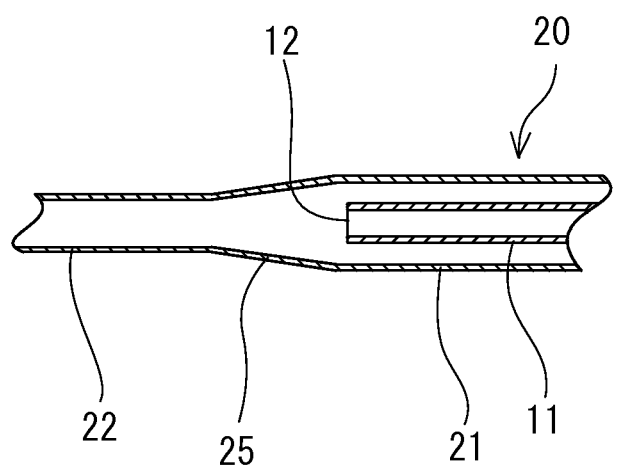
FIG. 2 is an enlarged sectional view of a neighborhood of a tapered part of the hollow needle of the living cell collection needle shown in FIG. 1.

The hollow needle 20 has the hollow body part 21 extended by the predetermined length and the hollow small-diameter front end part 22 extended from the hollow body part 21 toward the front end of the living cell collection needle 1. The hollow small-diameter front end part 22 is so formed that its length is shorter than that of the hollow body part 21 and its diameter is smaller than that of the hollow body part 21. More specifically, as shown in FIG. 2, because the hollow small-diameter front end part 22 is formed thinner than the hollow body part 21, the hollow small-diameter front end part has small outer and inner diameters. The hollow small-diameter front end part 22 is hollowly formed. Thereby the hollow needle 20 has a lumen penetrating therethrough from the front end (cutting edge part 24) of the hollow small-diameter front end part 22 to the rear end of the hollow body part 21.

The length of the hollow body part 21 is set to 200 to 400 mm and preferably 250 to 350 mm. The outer diameter thereof is set to 0.90 to 1.50 mm and preferably 1.10 to 1.35 mm. The inner diameter thereof is set to 0.70 to 1.30 mm and preferably 0.90 to 1.15 mm. The length of the hollow small-diameter front end part 22 is set to 25 to 80 mm and preferably 35 to 65 mm. The outer diameter thereof is set to 0.50 to 1.00 mm and preferably 0.6 to 0.9 mm. The inner diameter thereof is set to 0.25 to 0.80 mm and preferably 0.30 to 0.6 mm. Because the hollow needle 20 to be pierced into an ovary of a subject desiring to have her ova collected has the hollow small-diameter front end part 22, the subject is relieved from pain given thereto when an ovum collection operation is performed. Further the resistance to the piercing of the hollow needle 20 into the ovary of the subject is low when the collection operation is performed. Thereby it is possible to allow the collection operation to be easily performed. In the case where the hollow needle 20 has the hollow small-diameter front end part 22 thinner than the hollow body part 21, the hollow needle is capable of reducing the resistance to the piercing of the hollow needle 20 into the ovary of the subject.

As shown in FIGS. 1 and 2, the tapered part 25 is formed between the hollow body part 21 and the hollow small-diameter front end part 22. By providing the hollow needle 20 with the tapered part 25, the resistance to the piercing of the tapered part 25 into the ovary of the subject desiring to have her ova collected is much higher than the resistance to the piercing of the hollow small-diameter front end part 22 thereinto, it is possible to prevent the tapered part 25 from being pierced thereinto.

Figure 4:
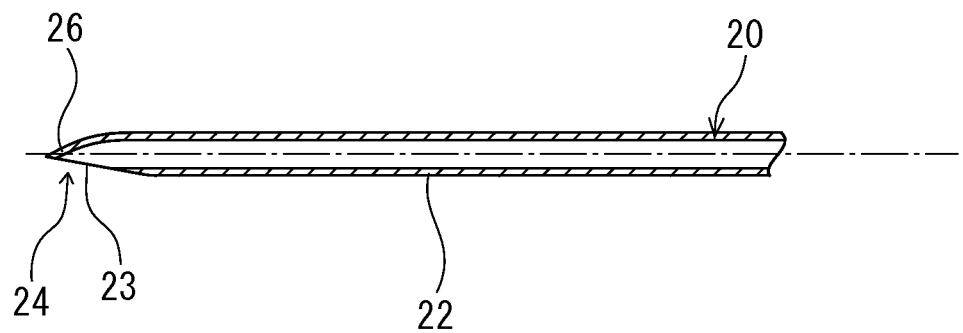
FIG. 4 is an enlarged sectional view of a front end portion of the hollow needle of the living cell collection needle shown in FIG. 1.
Figure 5:
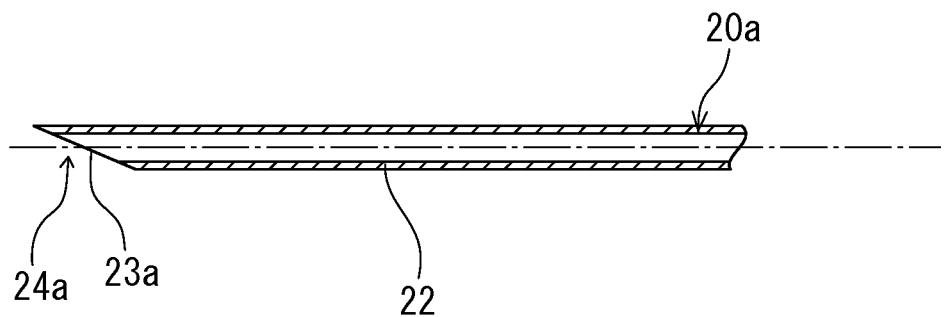
FIG. 5 is an enlarged sectional view of the front end portion of the hollow needle of another embodiment of the living cell collection needle of the present invention.

As shown in FIG. 4, a piercing cutting face 23 and the cutting edge part 24 acutely formed of the cutting face 23 are formed at the tip of the hollow small-diameter front end part 22. The cutting face 23 is obliquely extended in the direction of the central axis of the hollow needle 20. The cutting edge part 24 has a curved side portion 26 curved toward the cutting face 23. Because the cutting edge part 24 has the curved side portion 26, the cutting edge part 24 is displaced slightly from an extended line of a side surface of the hollow small-diameter front end part 22 toward the central axis of the hollow needle 20. By providing the cutting edge part 24 with the curved side portion 26, the cutting face 23 is almost parallel with the hollow needle 20 and has a sufficiently large opening area. Thereby the cutting face 23 allows the ovum collection operation to be easily performed. Although the cutting edge part 24 shown in FIG. 24 and described above is preferable, like a hollow needle 20a shown in FIG. 5, it is possible to form a cutting edge part 24a which is formed by obliquely cutting the hollow small-diameter front end part 22, does not have the curved side portion, and has a cutting face 23a cross the central axis of the hollow needle.

As a material to be used to form the hollow needle 20, a metal tube is used. As a metal, stainless steel is preferable. It is preferable to coat an outer surface of the hollow small-diameter front end part 22 with a low-friction substance. It is preferable not to coat the tapered part 25 and the hollow body part 21 with the low-friction substance. It is preferable to use silicone oil or silicone resin as the low-friction substance. The silicone oil conforming to the silicone oil standards (II: Medical Devices Division of Pharmaceutical Affairs Bureau No. 327, Ministry of Health and Welfare Pharmaceutical Affairs Bureau, Medical Care) or foreign standards equivalent to or higher than the above-described silicone oil standards are preferably used. As the silicone resin, a hardened material of a silicone solution containing dimethylpolysiloxane or the like as its main component is preferable. As the low-friction substance, it is possible to use fluorine-based resin, for example, PTFE (polytetrafluoroethylene) and ETFE (ethylene tetrafluoroethylene).

By coating the front end portion of the hollow needle to be pierced into the ovary of the subject desiring to have her ova collected with the low-friction substance, the subject is relieved from pain given thereto when the ovum collection operation is performed. Further the resistance to the piercing of the hollow needle into the ovary of the subject is low when the collection operation is performed. Thereby the collection operation can be performed easily. Because the tapered part 25 and the hollow body part 21 are not coated with the low-friction substance, the resistance to the piercing of the tapered part 25 into the ovary of the subject desiring to have her ova collected is much higher than the resistance to the piercing of the hollow small-diameter front end part 22 thereinto, it is possible to prevent the tapered part 25 from being pierced thereinto.

A coating tube 34 is fitted around the rear end portion of the hollow body part 21 of the hollow needle 20. A rear end 34a of the coating tube 34 is projected rearward from the rear end of the hollow needle 20. In other words, the rear end of the hollow needle 20 is positioned forward from the rear end of the coating tube 34 by a predetermined length. At the rear end of the coating tube 34, an annular space wider than the rear end portion of the hollow needle 20 is formed.

The inner tube 11 is a small-diameter tubular body having a lumen penetrating therethrough from its front end to its rear end. Most parts of the inner tube 11 are accommodated inside the hollow needle 20. In this embodiment, the inner tube 11 is so constructed as not to contact an inner surface of the hollow needle 20. The inner tube 11 is almost concentric with the hollow needle 20. A tubular lumen extended in an almost equal outer diameter and in an almost equal inner diameter is formed between an outer surface of the inner tube 11 and the inner surface of the hollow needle 20.

Figure 9:
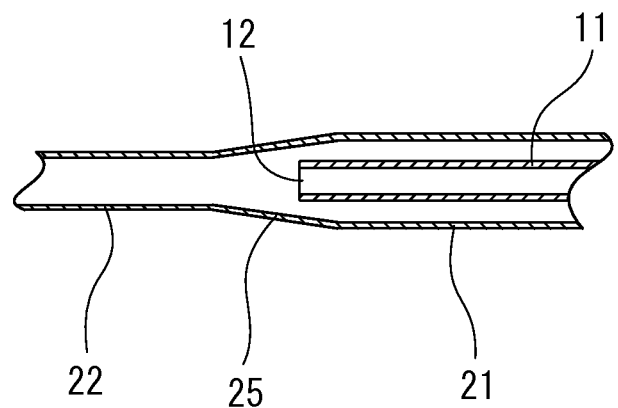
FIG. 9 is an enlarged sectional view of a neighborhood of the tapered part of the hollow needle of the living cell collection needle of another embodiment of the present invention.

In this embodiment, the inner tube 11 is extended in an almost equal inner diameter and in an almost equal outer diameter from its front end to its rear end. A front end 12 of the inner tube 11 is positioned inside the tapered part 25 of the hollow needle 20 or inside the front end portion of the hollow body part 21. As clearly shown in FIG. 2, in the living cell collection needle of this embodiment, the front end 12 of the inner tube 11 is positioned inside the front end portion of the hollow body part 21 of the hollow needle 20 and is proximate to a rear end of the tapered part 25. This construction prevents the inner tube 11 from interfering with the flow of a collection auxiliary liquid injected into the hollow needle 20. In addition, owing to this construction, during sucking of living cells (oocyte, ovum) into the inner tube 11, neither the hollow small-diameter front end part 22 of the hollow needle 20 nor the tapered part 25 interferes with the flow of the living cells. In addition, this construction prevents the living cells which have passed through the hollow small-diameter front end part 22 and the tapered part 25 from flowing between the hollow needle 20 and the inner tube 11 and allows the living cells to be securely sucked into the inner tube 11. As shown in FIG. 9, the front end 12 of the inner tube 11 may be positioned inside the tapered part 25 of the hollow needle 20.

The length of the inner tube 11 is set to 150 to 350 mm and preferably 200 to 300 mm. The outer diameter thereof is set to 0.50 to 1.00 mm and preferably 0.6 to 0.9 mm. The inner diameter thereof is set to 0.25 to 0.80 mm and preferably 0.30 to 0.6 mm. The difference between the inner diameter of the hollow body part 21 and the outer diameter of the inner tube 11 is set to preferably 0.1 to 0.4 mm and especially preferably 0.15 to 0.35 mm. It is preferable that the inner diameter of the inner tube 11 is almost equal to that of the hollow small-diameter front end part 22 or a little larger or smaller than that of the hollow small-diameter front end part 22. It is preferable that the difference between the inner diameter of the inner tube 11 and that of the hollow small-diameter front end part 22 is not more than 0.15 mm. It is preferable that the outer diameter of the inner tube 11 is almost equal to that of the hollow small-diameter front end part 22 or a little larger or smaller than that of the hollow small-diameter front end part 22. It is preferable that the difference between the outer diameter of the inner tube 11 and that of the hollow small-diameter front end part 22 is not more than 0.15 mm. As a material to be used to form the inner tube 11, a metal tube is used. As a metal, stainless steel is preferable.

A reinforcing tube 13 is fitted around the rear-end portion of the inner tube 11. A rear end of the reinforcing tube 13 terminates at a position forward from the rear end of the inner tube 11. In other words, the rear end of the inner tube 11 is projected rearward from the rear end of the reinforcing tube 13. The reinforcing tube 13 reinforces a portion of the inner tube projected from the hub 30. As a material to be used to form the reinforcing tube 13, a metal tube is used. As a metal, stainless steel is preferable. It is preferable to chamfer a front end surface of the inner tube 11 at its outer and inner edges. By so doing, it is possible to prevent the living cells to be sucked into the inner tube 11 from being damaged.

Figure 3:
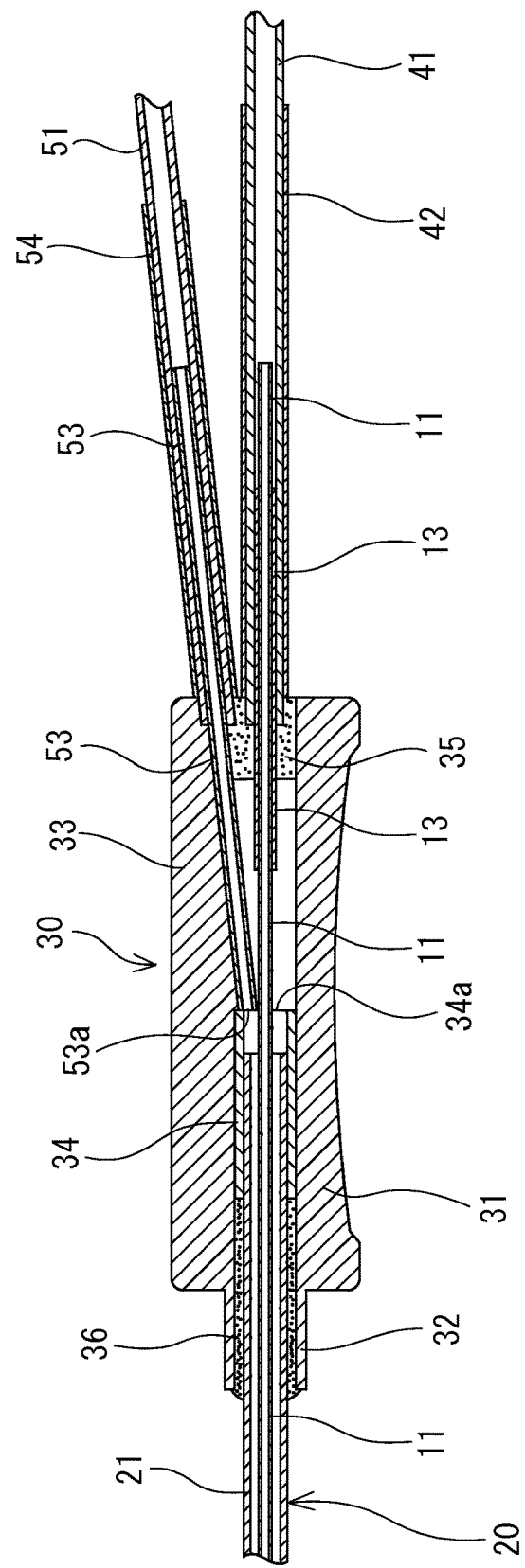
FIG. 3 is an enlarged sectional view of a neighborhood of a hub of the hollow needle of the living cell collection needle shown in FIG. 1.

As shown in FIG. 3, the hub 30 is a tubular member having a lumen penetrating therethrough from its front end to its rear end. The hub 30 has a hub body 31, a tubular projected part 32 projected forward from the front end of the hub body 31, and a marker 33 formed on a side portion of the hub body 31. The rear end portion of the hollow needle 20 coated with the coating tube 34 is accommodated inside the hub 30 and fixed to the hub 30 with a fixing agent 36. Thus the rear end of the hollow needle 20 and that of the coating tube are positioned inside the hub 30. The inner tube 11 is projected rearward from the rear end of the hollow needle 20, the coating tube 34, and the hub 30. As described above, the reinforcing tube 13 is fitted around the rear end portion of the inner tube 11. The rear end portion of the inner tube 11 around which the reinforcing tube is fitted is liquid-tightly fixed to the hub 30 with a fixing agent 35. The living cell sucking tube 41 is mounted on the rear end portion of the inner tube 11. The living cell sucking tube 41 is mounted on the inner tube 11 with the living cell sucking tube coating the rear end side of the reinforcing tube 13. As shown in FIG. 3, a front end of the living cell sucking tube 41 enters into the lumen of the hub 30 and is liquid-tightly fixed to the hub 30 with the fixing agent 35. In the living cell collection needle of this embodiment, a protection tube 42 is mounted on a front end portion of the living cell sucking tube 41 extended rearward from the hub 30.

As shown in FIG. 3, the lumen of the hub 30 has a tilted part extended gradually from its central portion toward its side portion with the tilted part being directed toward its rear end portion. A front side portion of the side tube 53 is inserted into the tilted part. A front end 53a of the side tube 53 is in contact with or proximate to the rear end (specifically, the rear end 34a of the coating tube 34) of the hollow needle 20. The side tube 53 is also liquid-tightly fixed to the hub 30 with the fixing agent 35. The collection auxiliary liquid supply tube 51 is mounted on a rear end portion of the side tube 53. The collection auxiliary liquid supply tube 51 is mounted on the side tube 53 with the collection auxiliary liquid supply tube 51 coating a rear end side of the side tube 53. As shown in FIG. 3, a front end of the collection auxiliary liquid supply tube 51 enters into the lumen of the hub 30 and is liquid-tightly fixed to the hub 30 with the fixing agent 35. In the living cell collection needle of this embodiment, a protection tube 54 is mounted on a front end side of the collection auxiliary liquid supply tube 51 extended from the hub 30.

As shown in FIG. 3, inside the hub 30, there is formed a lumen communicating with the inside of the side tube 53 and that of the hollow needle 20 and non-communicating with the inner tube 11. A front end of the side tube 53 is in contact with or proximate to the rear end (specifically, the rear end 34a of the coating tube 34) of the hollow needle 20. Thereby a liquid flowing out of the front end of the side tube 53 securely flows into the annular space disposed at the rear end portion of the coating tube 34 of the hollow needle 20, thus flowing into the space between the hollow needle 20 and the inner tube 11.

Figure 6:
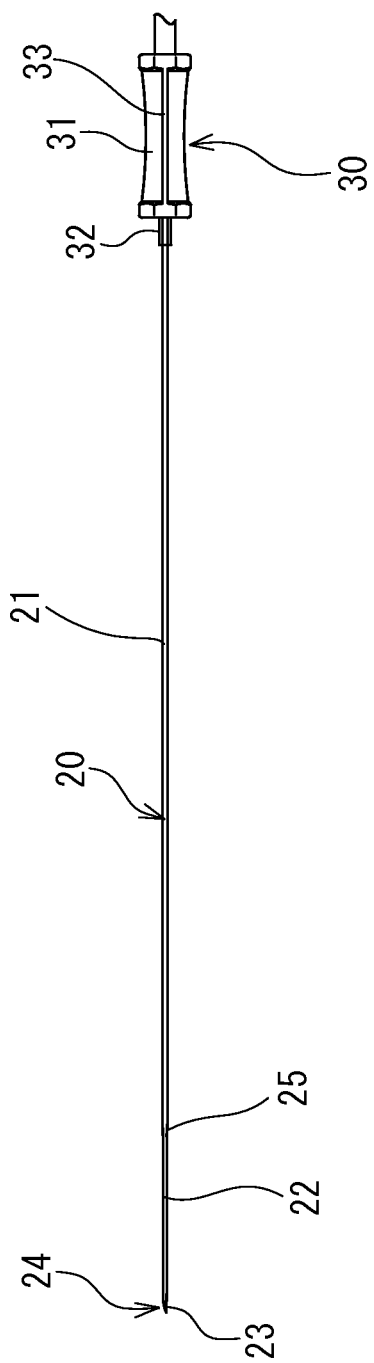
FIG. 6 is a plan view of the hollow needle and the hub of the living cell collection needle shown in FIG. 1.

As shown in FIGS. 1 and 6, the marker 33 associated with the direction of the cutting face 23 is formed on the periphery of the hub 30. The marker 33 of this embodiment is formed as a projected portion linearly extended from the front end of the hub 30 to the rear end thereof. The marker 33 is extended parallel to the central axis of the hollow needle 20. As shown in FIGS. 1 and 6, the cutting face 23 is formed by shifting it by a predetermined angle relative to the position of the marker 33 in the circumferential direction of the hollow needle 20. More specifically, the cutting face is formed by shifting it by approximately 90 degrees relative to the position of the marker 33 in the circumferential direction of the hollow needle 20. In other words, the marker 33 is formed by shifting it by a predetermined angle relative to the position of the cutting face 23 in the circumferential direction of the hub 30. More specifically, the marker is formed by shifting it by approximately 90 degrees relative to the position of the cutting face 23 in the circumferential direction of the hub 30. By forming the marker 33 on the periphery of the hub, the direction of the cutting face 23 can be easily checked. In the case of the living cell collection needle having the cutting face 23 formed by shifting it by approximately 90 degrees relative to the position of the marker 33 formed on the hub 30 in the circumferential direction of the hollow needle 20, the direction of the cutting face 23 can be easily checked.

As shown in FIGS. 1 and 6, in the living cell collection needle 1 of this embodiment, when the living cell collection needle 1 is held in a state where the hub 30 is positioned at the right side, the cutting edge part 24 is positioned at the left side, and the marker 33 faces upward, the cutting face 23 faces nearly the front. Thereby by holding the hub 30 (marker 33) in operating the living cell collection needle 1, the cutting face 23 faces the front of an ovum collection person. Thus it is easy to recognize the direction of the cutting face during an ovum collection operation. By recognizing the direction of the cutting face, it is easy to operate the living cell collection needle 1. A right-handed ovum collection person can easily perform the collection operation. The marker 33 of this embodiment is linearly formed as the projected portion extended from the front end of the hub 30 to the rear end thereof. But the marker of the present invention is not limited to the marker 33. It is possible to use markers having various forms so long as they allow the ovum collection person to check the direction of the cutting face 23.

Figure 7:
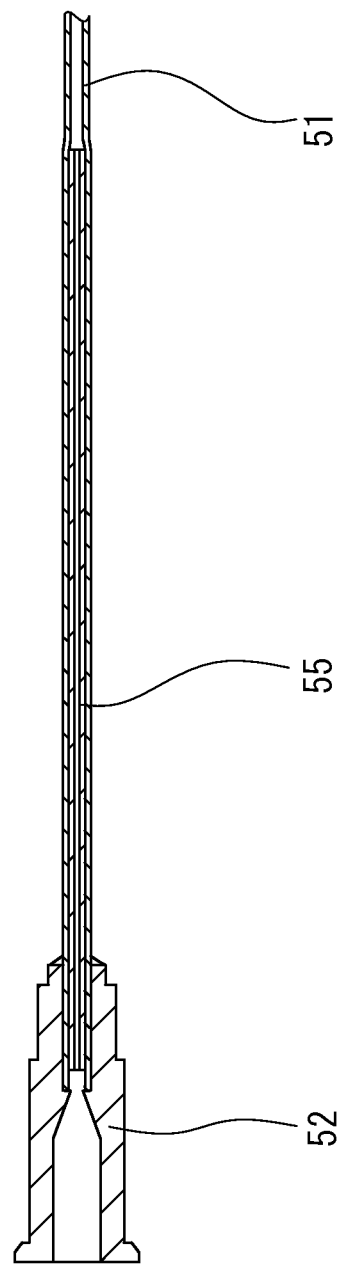
FIG. 7 is an enlarged sectional view of a neighborhood of a rear end portion of a collection auxiliary liquid supply tube of the living cell collection needle shown in FIG. 1.

As shown in FIGS. 1 and 7, a liquid supply means connection part 52 is fixed to a rear end portion of the collection auxiliary liquid supply tube 51. An inner surface of a rear end portion of the liquid supply means connection part 52 is so configured that the rear end portion thereof can be connected to a tip portion of a syringe. The collection auxiliary liquid supply tube 51 having the liquid supply means connection part 52 mounted thereon is capable of easily accomplishing liquid supply. The living cell collection needle 1 of this embodiment has a reinforcing member 55 extended by a predetermined length from the liquid supply means connection part 52 toward the front side of the tube 51. By providing the living cell collection needle with the reinforcing member 55, it is easy to perform an operation of connecting the collection auxiliary liquid supply tube and the liquid supply means connection part to each other and a liquid injection operation. As the reinforcing member 55, it is preferable to use a tubular body whose one end is positioned inside the liquid supply means connection part 52 and whose other end is extended into the rear end portion of the tube 51. It is possible to use a tubular body whose one end is fixed to an outer surface of the liquid supply means connection part 52 and whose other end is extended along an outer surface of the rear end portion of the tube 51. As the tubular body, a hard tubular body or a coil spring is preferable. As a material to be used to form the tubular body, a metal and synthetic resin can be used.

Figure 8:
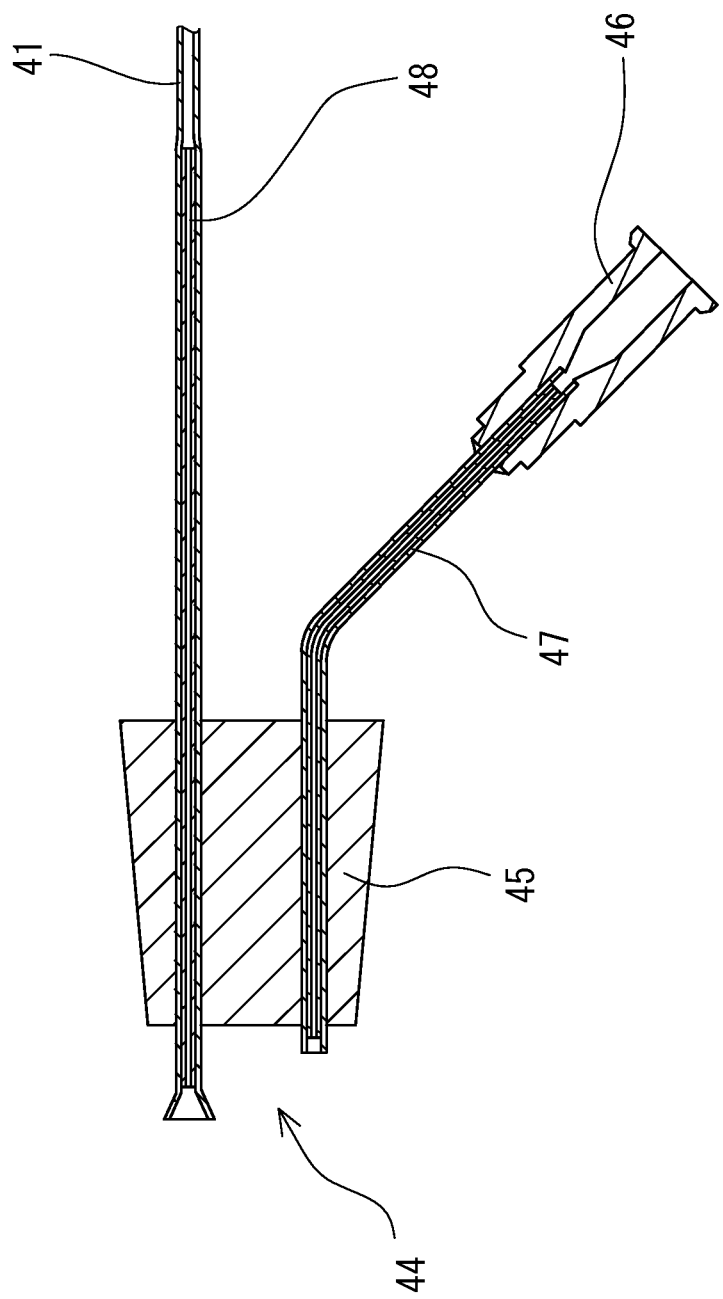
FIG. 8 is an enlarged sectional view of a neighborhood of a rear end portion of a living cell sucking tube of the living cell collection needle shown in FIG. 1.

As shown in FIGS. 1 and 8, a sucking means connection part 44 is mounted on the living cell sucking tube 41 at its rear end portion. In this embodiment, the sucking means connection part 44 has a plug body 45 to be mounted on an opening of a collection instrument and a sucking means mounting portion 46 mounted on the plug body 45. One end of the living cell sucking tube 41 is mounted on the inner tube 11 at its rear end. The other end of the living cell sucking tube 41 penetrates through the plug body 45. The other end of the living cell sucking tube 41 is formed as a diameter-enlarged portion. As shown in FIG. 8, there is provided a tube reinforcing member 48 extended forward from the rear end of the living cell sucking tube 41. The tube reinforcing member 48 penetrates through the plug body from the vicinity of the rear end of the living cell sucking tube 41 and is extended forward inside the tube 41 by a predetermined length. As the reinforcing member 48, a tubular body extended inside the tube 41 is preferable. As the reinforcing member 48, it is possible to use a tubular body extended along an outer surface of the rear end portion of the tube 41. As the tubular body, a hard tubular body or a coil spring is preferable. As a material to be used to form the tubular body, a metal and synthetic resin can be used.

The sucking means mounting portion 46 has a body and a shaft 47 extended from the body and penetrates through the plug body 45. The shaft 47 is bent. An inner surface of a rear end portion of the body of the sucking means mounting portion is so configured that the rear end portion thereof can be connected to a connector of a sucking device (not shown).

As materials to be used to form the plug body 45, it is possible to use synthetic rubber such as urethane rubber, silicone rubber, butadiene rubber; natural rubber such as latex rubber; elastomers such as polyolefin elastomer, polyamide elastomer, styrene elastomer (for example, styrene-butadiene-styrene copolymer, styrene-isoprene-styrene copolymer, styrene-ethylene butylene-styrene copolymer); and polyurethane. The living cell sucking tube 41 having the sucking means connection part 44 mounted thereon allows an ovum collection operation to be easily performed.

The living cell sucking tube 41 and the collection auxiliary liquid supply tube 51 are flexible tubular bodies each having an almost equal outer diameter and an almost equal inner diameter from its front end to its rear end. As materials to be used to form both tubes and the protection tubes, those having flexibility and toughness to some extent are preferable. Thus it is possible to use polyolefin (for example, polyethylene, polypropylene, ethylene-propylene copolymer); polyamide (for example, 6 nylon, 66 nylon); polyester (for example, polyethylene terephthalate); fluororesin (for example, PTFE, ETFE); synthetic rubber such as urethane rubber, silicone rubber, butadiene rubber; natural rubber such as latex rubber; and elastomer such as polyolefin elastomer, polyamide elastomer, styrene elastomer (for example, styrene-butadiene-styrene copolymer, styrene-isoprene-styrene copolymer, styrene-ethylene butylene-styrene copolymer); polyurethane; and especially thermoplastic polyurethane (thermoplastic polyether polyurethane and thermoplastic polyester polyurethane are preferable. Segmented thermoplastic polyether polyurethane having soft and hard segment portions is preferable. More specifically, as a main component of the soft segment, polytetramethylene ether glycol, polyethylene glycol, and polypropylene glycol are preferable. As a main component of the hard segment, 1,4-butanediol and the like are preferable.) The fluororesin (for example, PTFE, ETFE) are especially preferable.

The length of the tube 41 and that of the tube 51 are set to 100 to 700 mm and preferably 150 to 250 mm. The outer diameters thereof are set to 1.0 to 2.0 mm and preferably 1.46 to 1.79 mm. The inner diameters thereof are set to 0.7 to 1.5 mm and preferably 0.86 to 1.19 mm.

Figure 10:
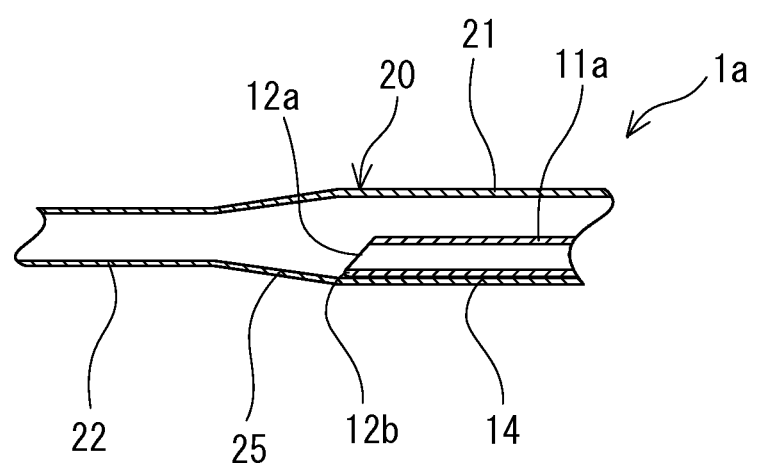
FIG. 10 is an enlarged sectional view of a neighborhood of the tapered part of the hollow needle of the living cell collection needle of still another embodiment of the present invention.

The inner tube 11 may be disposed inside a living cell collection needle 1a as shown in FIG. 10.

In the living cell collection needle 1a of this embodiment, an inner tube 11a has a portion (front portion) 14 which contacts the inner surface of the hollow needle 20 or is proximate thereto. More specifically, the inner tube 11a is not concentric (the central axes of the inner tube 11a and the hollow needle 20 are almost coincident with each other) with the hollow needle 20, but accommodated inside the hollow needle 20 with the inner tube 11a in contact with the inner wall of the hollow needle 20 or in proximity thereto. In this embodiment, the inner tube 11a has the portion (front portion) 14 which contacts the inner surface of the hollow needle 20. Thus a tubular (sectionally donut-shaped) lumen is not formed between the hollow needle 20 and the inner tube 11a, but a crescentic lumen is formed therebetween by cutting off a small perfect circle from a large perfect circle having a large section along the inner peripheral surface of the large perfect circle. By so doing, the lumen formed between the hollow needle and the inner tube has a comparatively large width (height).

A front end 12a of the inner tube 11a is formed as a tilted open portion oblique by a predetermined angle to the central axis of the inner tube in which the portion 14 that contacts the inner surface of the hollow needle or is proximate thereto is disposed at a back side. More specifically, in the living cell collection needle 1a of this embodiment, the front end opening 12a of the inner tube 11a is formed as the tilted open portion oblique by the predetermined angle to the central axis of the inner tube 11a. In this embodiment, the front end opening 12a is formed by disposing the portion 14 which contacts the inner surface of the hollow needle or is proximate thereto at the back side. Therefore the front end opening 12a faces the wide portion of the above-described crescentic lumen. In other words, the front end opening 12a faces the central axis of the hollow needle 20. In this embodiment, the front end opening 12a faces toward the central axis of the tapered part 25. As shown in FIG. 10, a tip 12b of the front end opening 12a of the inner tube 11a is formed of a front end of the portion 14 which contacts the inner surface of the hollow needle or is proximate thereto. The tip 12b is positioned at the rear end portion of the tapered part 25 or at the front end portion of the hollow body part 21. The tip 12b shown in FIG. 10 is positioned at a boundary between the tapered part 25 and the hollow body part 21. The above-described construction allows the living cells to be easily sucked into the inner tube 11a and the collection auxiliary liquid to be easily injected into the hollow needle. As with the above-described embodiment, it is preferable to chamfer outer and inner edges of the front end surface of the inner tube 11a. By so doing, it is possible to prevent the living cells to be sucked into the inner tube 11a from being damaged.

In the living cell collection needle 1a having the above-described form of accommodating the inner tube 11a therein, the construction of the inside of the hub 30 as shown in FIG. 11 is acceptable.

As shown in FIG. 11, the hub 30 is a tubular member having a lumen penetrating therethrough from its front end to its rear end as with the above-described embodiment. The hub 30 has the hub body 31, the tubular projected part 32 projected forward from the front end of the hub body 31, and the marker 33 formed on the side portion of the hub body 31. The rear end portion of the hollow needle 20 coated with the coating tube 34 is accommodated inside the hub 30 and fixed to the hub 30 with the fixing agent 36. Thus the rear end of the hollow needle 20 and that of the coating tube are positioned inside the hub 30.

The inner tube 11a is projected rearward from the rear end of the hollow needle 20, the coating tube 34, and the hub 30. The reinforcing tube 13 is fitted around the rear end portion of the inner tube 11a. The rear end portion of the inner tube 11a around which the reinforcing tube is fitted is liquid-tightly fixed to the hub 30 with the fixing agent 35. The living cell sucking tube 41 is mounted on the rear end portion of the inner tube 11a. The living cell sucking tube 41 is mounted on the inner tube 11a with the living cell sucking tube coating the rear end side of the reinforcing tube 13. As shown in FIG. 11, the front end of the living cell sucking tube 41 enters into the lumen of the hub 30 and is liquid-tightly fixed to the hub 30 with the fixing agent 35. In the living cell collection needle of this embodiment, the protection tube 42 is mounted on the front end portion of the living cell sucking tube 41 extended rearward from the hub 30. The inner tube 11a is positioned nearer to a peripheral side of the hub 30 than the inner tube of the above-described embodiment. Thus the interval between the inner tube 11a and the side tube is longer than that between the inner tube 11 of the above-described embodiment and the side tube.

As shown in FIG. 11, the lumen of the hub 30 has a tilted part extended gradually from its central portion toward its side portion with the tilted part being directed toward its rear end portion. The front side portion of the side tube 53 is inserted into the tilted part of the lumen. In the living cell collection needle of this embodiment, as shown in FIG. 11, the front end 53a of the side tube 53 enters into the rear end portion of the hollow needle 20. More specifically, the front end 53a of the side tube 53 enters into the rear end portion of the coating tube 34 (slightly more inward than the rear end 34a). The above-described construction allows the collection auxiliary liquid to be easily injected into the hollow needle 20. The side tube 53 is also liquid-tightly fixed to the hub 30 with the fixing agent 35. The front end of the side tube 53 may enter into the rear end portion of the hollow needle 20. The collection auxiliary liquid supply tube 51 is mounted on the rear end portion of the side tube 53. The collection auxiliary liquid supply tube 51 is mounted on the side tube 53 with the collection auxiliary liquid supply tube 51 coating the rear side of the side tube 53 and is liquid-tightly fixed to the hub 30 with the fixing agent 35. The protection tube 54 is mounted on the front end side of the collection auxiliary liquid supply tube 51 extended from the hub 30.

INDUSTRIAL APPLICABILITY

The living cell collection needle of the present invention is constructed as described below.

(1) A living cell collection needle for collecting oocytes or ova from a human ovary, comprising a hollow needle having a hollow body part extended by a predetermined length, a hollow small-diameter front end part extended from said hollow body part toward a front end of said living cell collection needle and having a shorter length and a smaller diameter than said hollow body part, a tapered part positioned between said hollow small-diameter front end part and said hollow body part and decreasing toward said hollow small-diameter front end part in outer and inner diameters thereof, and a piercing cutting edge part formed at a front end of said hollow small-diameter front end part; a hub fixed to a rear end portion of said hollow body part of said hollow needle; an inner tube which is accommodated inside said hollow needle, whose front end is positioned inside said tapered part or inside a front end portion of said hollow body part, and whose rear end portion penetrates through said hub and is fixed to said hub; and a living cell sucking tube connected to a rear end portion of said inner tube, wherein a rear end of said hollow needle is positioned inside said hub; said living cell collection needle has a side tube whose front end portion is positioned inside said hub and communicates with said inside of said hollow needle and whose rear end portion projects rearward from said hub and is liquid-tightly fixed to said hub; and a collection auxiliary liquid supply tube is connected to said side tube.

In the living cell collection needle of the present invention, the front end portion of the hollow needle is formed as the hollow small-diameter front end part. Thus the subject is relieved from pain given thereto when the ovum collection operation is performed. Further the resistance to the piercing of the hollow needle 20 into the ovary of the subject is low when the collection operation is performed. Thereby it is possible to easily perform the collection operation. Furthermore after the collection needle is inserted into the ovary, the living cell collection needle is capable of easily supplying (injecting) the collection auxiliary liquid to the ovary. After the supply of the collection auxiliary liquid to the ovary is stopped, owing to the operation of the living cell sucking tube, the living cell collection needle is capable of securely collecting oocytes and ova together with the collection auxiliary liquid injected into the ovary.

The embodiments of the living cell collection needle may be as described below.

(2) A living cell collection needle according to the above (1), wherein said front end of said inner tube is positioned inside said front end portion of said hollow body part of said hollow needle and is proximate to a rear end of said tapered part.

(3) A living cell collection needle according to the above (1), wherein said front end of said inner tube is positioned inside said tapered part of said hollow needle.

(4) A living cell collection needle according to any one of these above (1) through (3), wherein said inner tube is a metal tube.

(5) A living cell collection needle according to any one of these above (1) through (4), wherein said rear end portion of said inner tube is fixed to said hub.

(6) A living cell collection needle according to any one of these above (1) through (5), wherein said inner tube has a reinforcing tube fitted around said rear end portion thereof and is liquid-tightly fixed to said hub at said rear end portion thereof around which said reinforcing tube is fitted.

(7) A living cell collection needle according to any one of these above (1) through (6), wherein said hollow small-diameter front end part is coated with a low-friction substance; and said hub has a marker associated with a direction of a piercing cutting face of said piercing cutting edge part.

In the living cell collection needle of the present invention, because the hollow small-diameter front end part is coated with the low-friction substance, the subject can be relieved from pain given thereto when the ovum collection operation is performed. Because the hub has the marker associated with the direction of the piercing cutting face, the direction of the cutting face can be easily checked, which allows ova to be easily collected into the cutting edge part.

(8) A living cell collection needle according to any one of these above (1) through (7), wherein said cutting edge part has a curved side portion curved toward a piercing cutting face.

(9) A living cell collection needle according to any one of these above (1) through (8), wherein said inner tube has a portion which contacts an inner surface of said hollow needle or is proximate thereto; and a front end of said inner tube is formed as a tilted open portion oblique by a predetermined angle to a central axis of said inner tube in which said portion that contacts said inner surface of said hollow needle or is proximate thereto is disposed at a back side.

The invention claimed is:

1. A living cell collection needle for collecting oocytes or ova from a human ovary, comprising:
a hollow needle having a hollow body part extended by a predetermined length, a hollow small-diameter front end part extended from said hollow body part toward a front end of said living cell collection needle and having a shorter length and a smaller diameter than said hollow body part, a tapered part positioned between said hollow small-diameter front end part and said hollow body part and decreasing toward said hollow small-diameter front end part in outer and inner diameters of said tapered part, and a piercing cutting edge part formed at a front end of said hollow small-diameter front end part;

a hub fixed to a rear end portion of said hollow body part of said hollow needle;

an inner tube which is accommodated inside said hollow needle, said inner tube having a rear end portion that penetrates through said hub and is fixed to said hub;

a living cell sucking tube connected to a rear end portion of said inner tube, wherein a rear end of said hollow needle is positioned inside said hub;

said living cell collection needle has a side tube, said side tube having a front end portion positioned inside said hub and communicating with said inside of said hollow needle and said side tube having a rear end portion that projects rearward from said hub and is liquid-tightly fixed to said hub;

a collection auxiliary liquid supply tube connected to said side tube;

said inner tube has an outer diameter smaller than an inner diameter of said hollow body part of said hollow needle, said living cell collection needle has a lumen formed between an outer surface of said inner tube and an inner surface of said hollow body part of said hollow needle, a front end of said inner tube is positioned inside said tapered part or inside a front end portion of said hollow body part, a front portion of said inner tube contacts said inner surface of said hollow needle or is proximate to said inner surface of said hollow needle; and said front end of said inner tube has a tilted open portion oblique by a predetermined angle to a central axis of said inner tube, and said lumen has a crescent cross section at said front portion of said inner tube, said crescent cross section having a form of a smaller circle cut out from a larger circle along an inner peripheral surface of said larger circle, and wherein said crescent cross section has a wide portion and said tilted portion faces said wide portion of said crescent cross section.

2. The living cell collection needle according to claim 1, wherein said front end of said inner tube is positioned inside said front end portion of said hollow body part of said hollow needle and is proximate to a rear end of said tapered part.

3. The living cell collection needle according to claim 1, wherein said front end of said inner tube is positioned inside said tapered part of said hollow needle.

4. The living cell collection needle according to claim 1, wherein said inner tube is a metal tube.

5. The living cell collection needle according to claim 1, wherein said inner tube has a reinforcing tube fitted around said rear end portion of said inner tube and is liquid-tightly fixed to said hub at said rear end portion of said inner tube around which said reinforcing tube is fitted.

6. The living cell collection needle according to claim 1, wherein said hollow small-diameter front end part is coated with a low-friction substance; and said hub has a marker associated with a direction of a piercing cutting face of said piercing cutting edge part.

7. The living cell collection needle according to claim 1, wherein said piercing cutting edge part has a curved side portion curved toward a piercing cutting face.

8. The living cell collection needle according to claim 1, wherein said front portion of said inner tube contacts said inner surface of said hollow needle, and said front end of said inner tube is positioned inside said front end portion of hollow body part.

9. The living cell collection needle according to claim 1, wherein an outer edge and an inner edge of a front end surface of said inner tube is chamfered.

10. The living cell collection needle according to claim 1, wherein said hollow needle is a metal tube.

11. The living cell collection needle according to claim 1, wherein a difference between said inner diameter of said hollow body and said outer diameter of said inner tube is 0.1 mm to 0.4 mm, said inner diameter of said hollow body being 0.70 mm to 1.30 mm, and said outer diameter of said inner tube being 0.50 to 1.00 mm.

12. A living cell collection needle for collecting oocytes or ova from a human ovary, comprising:

a hollow needle having a hollow body part extended by a predetermined length, a hollow small-diameter front end part extended from said hollow body part toward a front end of said living cell collection needle and having a shorter length and a smaller diameter than said hollow body part, a tapered part positioned between said hollow small-diameter front end part and said hollow body part and decreasing toward said hollow small-diameter front end part in outer and inner diameters of said tapered part, and a piercing cutting edge part formed at a front end of said hollow small-diameter front end part;

a hub fixed to a rear end portion of said hollow body part of said hollow needle;

an inner tube which is accommodated inside said hollow needle, said inner tube having a rear end portion that penetrates through said hub and is fixed to said hub;

a living cell sucking tube connected to a rear end portion of said inner tube, wherein a rear end of said hollow needle is positioned inside said hub;

said living cell collection needle has a side tube, said side tube having a front end portion positioned inside said hub and communicating with said inside of said hollow needle and said side tube having a rear end portion that projects rearward from said hub and is liquid-tightly fixed to said hub;

a collection auxiliary liquid supply tube connected to said side tube;

said inner tube has an outer diameter smaller than an inner diameter of said hollow body part of said hollow needle, said living cell collection needle has a lumen formed between an outer surface of said inner tube and an inner surface of said hollow body part of said hollow needle, a front end of said inner tube is positioned inside said tapered part or inside a front end portion of said hollow body part, a front portion of said inner tube contacts said inner surface of said hollow needle or is proximate to said inner surface of said hollow needle;

a front end of said inner tube has a tilted open portion oblique by a predetermined angle to a central axis of said inner tube; and an outer edge and an inner edge of a front end surface of said inner tube being chamfered.

13. The living cell collection needle according to claim 12, wherein said front end of said inner tube is positioned inside said front end portion of said hollow body part of said hollow needle and is proximate to a rear end of said tapered part.

14. The living cell collection needle according to claim 12, wherein said front end of said inner tube is positioned inside said tapered part of said hollow needle.

15. The living cell collection needle according to claim 12, wherein said inner tube is a metal tube.

16. The living cell collection needle according to claim 12, wherein said hollow needle is a metal tube.

17. The living cell collection needle according to claim 12, wherein said inner tube has a reinforcing tube fitted around said rear end portion of said inner tube and is liquid-tightly fixed to said hub at said rear end portion of said inner tube around which said reinforcing tube is fitted.

18. The living cell collection needle according to claim 12, wherein said hollow small-diameter front end part is coated with a low-friction substance, and said hub has a marker associated with a direction of a piercing cutting face of said piercing cutting edge part.

19. The living cell collection needle according to claim 12, wherein said piercing cutting edge part has a curved side portion curved toward a piercing cutting face.

20. The living cell collection needle according to claim 12, wherein said front portion of said inner tube contacts said inner surface of said hollow needle, and said front end of said inner tube is positioned inside said front end portion of hollow body part.

* * * * *